(12) United States Patent
Schaepman et al.

(10) Patent No.: US 7,002,346 B2
(45) Date of Patent: Feb. 21, 2006

(54) METHOD FOR ACCURATE DETERMINATION OF SAMPLE TEMPERATURE IN A NMR CHECK WEIGHING SYSTEM

(75) Inventors: Alexander Schaepman, Breda (NL); Vincent Bons, Geldrop (NL); Paulus C. J. M. Hendrickx, Baarle-Nassau (NL); Jozef A. W. M. Corver, Nuenen (NL)

(73) Assignee: The BOC Group, Inc., Murray Hill, NJ (US)

( * ) Notice: Subject to any disclaimer, the term of this patent is extended or adjusted under 35 U.S.C. 154(b) by 16 days.

(21) Appl. No.: 10/881,930

(22) Filed: Jun. 30, 2004

(65) Prior Publication Data

US 2005/0242811 A1   Nov. 3, 2005

Related U.S. Application Data

(60) Provisional application No. 60/567,708, filed on May 3, 2004.

(51) Int. Cl.
*G01V 3/00* (2006.01)

(52) U.S. Cl. .................. 324/315; 324/300; 177/50; 374/102

(58) Field of Classification Search .............. 177/50; 324/315, 300; 374/102
See application file for complete search history.

(56) References Cited

U.S. PATENT DOCUMENTS

| | | | |
|---|---|---|---|
| 3,796,873 A | 3/1974 | Ledgett | |
| 4,727,325 A | 2/1988 | Matsui et al. | |
| 5,015,954 A | 5/1991 | Dechene et al. | |
| 5,049,819 A | 9/1991 | Dechene et al. | |
| 5,291,422 A | 3/1994 | Esztergar | |
| 5,302,897 A | 4/1994 | Dechene et al. | |
| 5,818,228 A | * 10/1998 | Menon et al. | .............. 324/300 |

(Continued)

FOREIGN PATENT DOCUMENTS

DE            1803372 A1      5/1970

(Continued)

OTHER PUBLICATIONS

Darros-Barbosa, R et al., "Temperature and Concentration Dependence of Heat Capacity of Model Aqueous Solutions", Int'l Journal of Food Properties, vol. 6, pp. 239-258, 2003.*

(Continued)

*Primary Examiner*—Michael Tokar
*Assistant Examiner*—Jeremiah Shipman
(74) *Attorney, Agent, or Firm*—Ira Zebrak; Bernard Lau

(57) ABSTRACT

A method (10) permits determining the temperature in a magnetic resonance check weighing system (24) of a sample in a container (22) on a production line at the time of magnetic resonance testing. Method (10) includes the steps of determining a time-temperature correction factor for the sample in the container (50), measuring the temperature of the composite sample and the container at a time other than the time of magnetic resonance testing (70), and applying the correction factor to the temperature of the composite sample and container at a time other than the time of magnetic resonance testing (80).

11 Claims, 3 Drawing Sheets

U.S. PATENT DOCUMENTS

| | | |
|---|---|---|
| 6,028,428 A | 2/2000 | Cunningham et al. |
| 6,166,542 A * | 12/2000 | Gallop et al. ............... 324/300 |
| 6,362,619 B1 | 3/2002 | Prammer et al. |
| 6,377,049 B1 | 4/2002 | Benz et al. |
| 6,426,058 B1 | 7/2002 | Pines et al. |
| 6,541,974 B1 * | 4/2003 | Schutz ...................... 324/321 |
| 6,759,601 B1 * | 7/2004 | Petty et al. .................... 177/1 |
| 2004/0231699 A1 | 11/2004 | Corver |
| 2004/0251904 A1 | 12/2004 | Corver et al. |

FOREIGN PATENT DOCUMENTS

| | | |
|---|---|---|
| GB | 2149509 A | 6/1985 |
| GB | 2400440 A * | 10/2004 |
| WO | WO 99/67606 A1 | 12/1999 |

OTHER PUBLICATIONS

Roger Darros-Barbosa, Murat O. Balaban, Arthur A. Teixera; Temperature and Concentration Dependence of Heat Capacity of Model Aqueous Solutions, International Journal of Food Properties, vol. 6, No. 2, pp. 239-258, 2003.

Derwent WPI Abstract, UNILEVER NV, Package Weight Measuring System, NL 154001B, Jul. 15, 1977 (Corresponds to DE 1803372A1).

* cited by examiner

METHOD FOR ACCURATE DETERMINATION OF SAMPLE TEMPERATURE IN A NMR CHECK WEIGHING SYSTEM

CROSS REFERENCE TO RELATED APPLICATION

This application claims the benefit of the filing date of U.S. Provisional Application Ser. No. 60/567,708, filed May 3, 2004, which is incorporated herein by reference.

FIELD OF THE INVENTION

The present invention relates to check weighing material in a container, while the container is moving in a production line, using nuclear magnetic resonance (NMR) techniques. More particularly, the present invention relates to a method for accurate determination of the temperature of the material in the container at the time of a NMR check weighing measurement.

BACKGROUND

The use of NMR techniques in measurement, detection and imaging has become desirable in many scientific fields of endeavor. The non-invasive, non-destructive nature of NMR has facilitated application to industrial instrumentation, analysis and control tasks, in a variety of applications, including but not limited to cosmetics, perfumes, industrial chemicals, biological samples and food products. As one example, check weighing is used by the pharmaceuticals industry for monitoring and regulating the amount of drug in a sealed glass vial during filling. The drug weight can be as small as a fraction of a gram, and is required to be weighed with an accuracy of a few percent or better, in a vial weighing tens of grams at a rate of several weighings per second.

International Patent Application No. WO 99/67606, incorporated herein by reference as if fully written out below, describes a check weighing system for samples on a production line using NMR techniques. This system includes a magnet for creating a static magnetic field over an interrogation zone to produce a net magnetisation within a sample located within the interrogation zone, and a RF coil for applying an alternating magnetic field over the interrogation zone to cause excitation of the sample according to the principles of NMR.

As is well known in the NMR art, after pulse excitation of the sample by the alternating magnetic field, the sample emits a signal induced in the RF coil, called the free induction decay ("FID"), from which much information, like sample mass (or weight) can be learned. The temperature of the sample exerts a great influence on molecular activity of the sample, and, in turn its FID. For example, a change in temperature of the sample alters the rate of molecular motion, also altering the effective strength of the dipole—dipole interaction., i.e., proton relaxation, that is central to a nuclear magnetic resonance interaction and emission of the FID. Moreover, if the sample excitation produces incomplete magnetization in the sample at the time of the sample's magnetic resonance measurement, the temperature influence on the magnetization process itself greatly enhances the effect of temperature variations in the sample. Consequently, if the sample mass or weight (hereinafter referred to as "sample weight") is to be determined with accuracy and precision, the temperature of the sample at the time of its magnetic resonance measurement must be accurately measured or determined.

A direct measurement would seem most advantageous to find the temperature of the sample at the time of its magnetic resonance measurement. However, as noted above, the principals of magnetic resonance measurement require that at the moment of measurement the sample be positioned in both the interrogation zone and the alternating magnetic field region of the RF coil. This geometry, and the essential need for magnetic field homogeneity, makes it very impracticable to place one or more temperature sensor devices so that the temperature of the sample may be accurately measured at the time of magnetic resonance measurement of the sample.

This leaves the alternative of measuring sample temperature at some point on the moving production line either before or after the interrogation zone, and using that information to find the required sample temperature at the time of its magnetic resonance measurement. Previously in the art sample temperature was measured at the sample filling station, and the sample temperature assumed to be constant between the times of temperature measurement time and magnetic resonance measurement. Because sample temperature does vary during this time interval, such NMR sample weight determinations were less accurate.

It is desirable to provide a method for more accurately determining the temperature of samples on a production line in a NMR check weighing system at the time the magnetic resonance measurement of the sample is made.

SUMMARY

There is provided a method for determining the temperature in a magnetic resonance check weighing system of a sample in a container on a production line at the time of magnetic resonance testing, comprising the steps of:

determining a time-temperature correction factor for the sample in the container;

measuring the temperature of the composite sample and the container at a time other than the time of magnetic resonance testing, and applying the correction factor to the temperature of the composite sample and container at a time other than the time of magnetic resonance testing.

DETAILED DESCRIPTION

Figure 2:
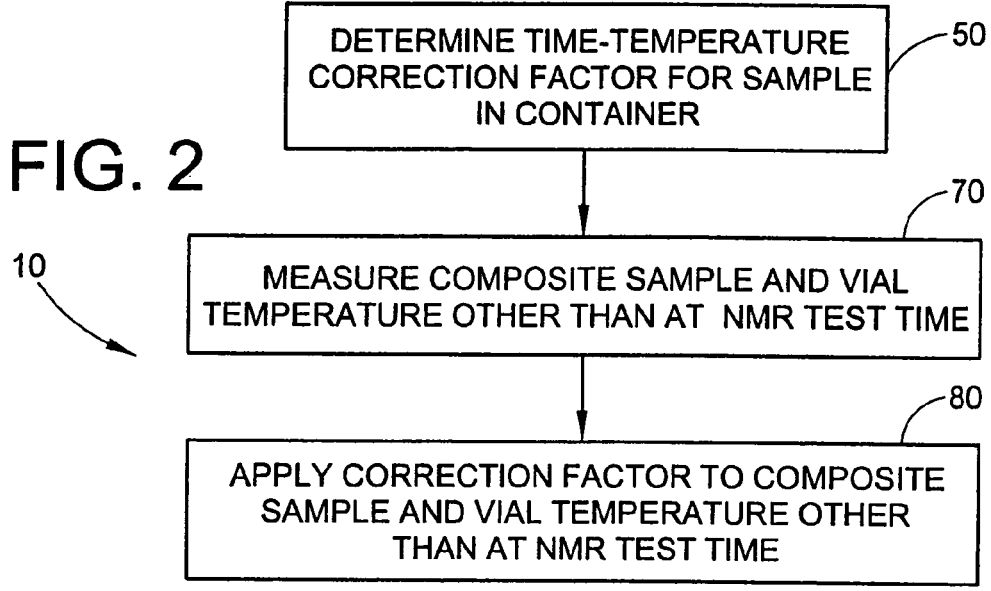
FIG. 2 is a top level flow chart of an exemplary method in accordance with the teachings of the present invention for accurate determination of the temperature of the product in the container at the time of a NMR check weighing measurement.

A method in accordance with the present invention is indicated generally by the numeral 10 in FIG. 2. This method is used in a non-contact, NMR check weighing system 20 that checks the weight of the content of a container while continuously moving in a production line (also known as a "product filling line"). One exemplary application requiring such check weighing is the packaging of pharmaceuticals. In order to understand best this method, it is helpful to first review certain of the structure of an exemplary NMR check weighing system and its associated production line.

Exemplary NMR Check Weighing System for Pharmaceutical Packaging

Figure 1:
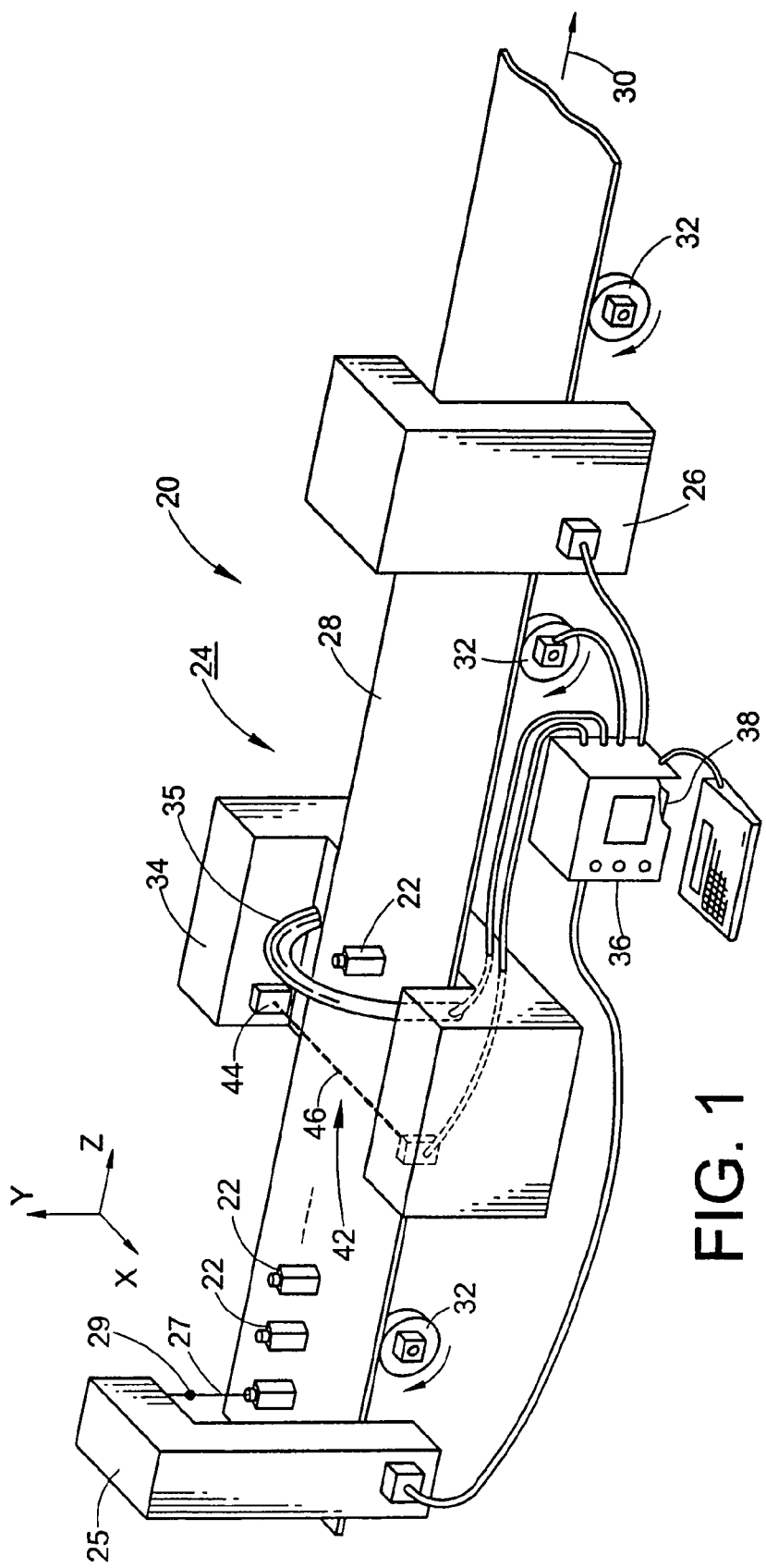
FIG. 1 is a perspective view of a portion of a production line with an exemplary NMR check weighing station for checking that each container passing through the weighing station has the desired amount of product.

FIG. 1 shows a portion of a production line, which fills glass vials 22 with a drug sample. The exemplary check weighing station 24 is provided "in-line" for non-contact weighing of each of the filled vials that pass therethrough, and a reject station 26 that removes those vials from the line that do not have the sufficient amount of the drug to meet product specifications. Vials 22 are transported to check weighing station 24 from a filling (and optionally sealing) station 25 (shown in FIG. 2) by a conveyor having a conveyor belt 28 which, as represented by the arrow 30, moves in the z direction through the action of rotating conveyor wheels 32.

Filling station 25 may include a filling needle 27 or other device to carry the sample into vial 22 and temperature sensors 29 as further explained below. A plurality of vials 22 may be filled simultaneously at filling station 25. Temperature sensors 29 may include sensors to measure the temperature of vial 22 glass, and the temperature of the sample at a plurality of locations within the volume of the sample.

Check weighing station 24 uses NMR techniques to determine the mass of the drug sample within each of the vials 22. As those ordinarily skilled in the art will appreciate, glass vials are useful as the container, because they do not give a signal that might interfere with the measurement process. In this embodiment, check weighing station 24 includes a source of a static magnetic field such as an electromagnet or a permanent magnet 34, RF probe 35, and a computer control system 36 having a processor 38. Magnet 34 creates a homogeneous direct current (DC) or static magnetic field in the x direction across conveyor belt 28 in a region that may be referred to as the interrogation zone 40. Interrogation zone 40 extends the length of conveyor belt 28 through which the static magnetic field is uniformly applied by permanent magnet 34. The sample in vial 22 contains nuclei which each possess a magnetic moment, e.g. 1H nuclei (protons), as a result of the spin of the nuclei. Because the sample protons posses a magnetic moment, the sample is capable of acquiring a net magnetisation when under the influence of certain magnetic fields. When the sample is within interrogation zone 40, the applied static magnetic field creates a net magnetisation within the sample. A vial position detection device 42 preceding or at the start of interrogation zone 40 (such as the optical position sensor 44 having a light beam 46) detects when vial 22 reaches a known physical position on conveyor belt 28 preceding check weighing station 24.

In most NMR systems, the static magnetic field strength is such that the Larmor frequency of the sample is in the radio frequency range of the electromagnetic spectrum. Applying an alternating current (AC) magnetic field to the sample at the sample's Larmor frequency and orientated orthogonal to the static magnetic field, will cause the sample's net magnetisation to rotate about the AC magnetic field's axis, away from the direction of the static field. In this embodiment, this magnetic field is generated by applying a corresponding AC current to the RF probe 35. Varying the amount of energy delivered to the RF probe 35 can vary the angle of rotation of the net magnetisation.

In this exemplified embodiment, an excitation field that causes a 90° rotation is used to excite the sample. After the 90° pulse has been applied to the sample, the sample is left in a high-energy, non-equilibrium state, from which it will relax back to its original state of equilibrium. As it relaxes, electromagnetic energy at the Larmor frequency is emitted, the magnetic component of which induces a sample reply signal known as the Free Induction Delay ("FID") in the form of current in the RF probe 35.

RF probe 35 monitors energy emitted by the sample as the net magnetisation of the sample returns to its original state and generates an output signal having a characteristic which is proportional to the energy emitted. In the present example a characteristic of the induced current, i.e., amplitude, varies with, among other things, the number of magnetic moments in the sample and hence the number of molecules in the sample. The received signal is then passed to the computer control system 36, which compares the amplitude of the signal received from the unknown sample, with the amplitude of a signal received from a calibration sample with a known weight, to determine the weight of the sample being tested.

For illustrative purposes, but not by way of limitation, the general operation of the NMR check weighing system 24 as shown in FIG. 1 will be described. First, check weighing system 24 is initialized, including installing a RF probe 35 appropriate for the sample to be tested. Once production is begun, conveyor belt 28 continuously transports vials 22 whose sample weight is to be determined. Vials 22 are filled at filling station 25, and the temperature of the vial glass and sample measured using temperature sensors 29 and recorded by computer control system 36. As each vial 22 reaches a position detected by optical position sensor 44, optical position sensor 44 generates a signal establishing the position of that vial 22 to computer control system 36. Computer control system 36 then tracks the motion of conveyor belt 28 as vial 22 advances to the position $P_M$ within interrogation zone 40, where the sample in vial 22 is measured by magnetic resonance.

At the instant in time when vial 22 is in position $P_M$, a brief energization of RF probe 35 is triggered, applying an alternating magnetic field in interrogation zone 40 such that the net magnetisation of the sample in vial 22 is temporarily changed. RF probe 35 monitors the energy emitted by the sample in vial 22 as the net magnetisation of the sample returns to its original state of equilibrium, and generates an output signal having a characteristic which is proportional to the energy emitted, such as current amplitude. Computer control system 36 receives the RF probe 35 output signal. As further explained below, processor 38 determines the sample temperature at the time energization of RF probe 35 concludes. Processor 38 uses this accurate sample temperature, and compares the current amplitude or other output signal characteristic with like data obtained from at least one similar sample of known mass, and determines the mass of the sample from the results of the comparison.

Sample Temperature Compensation

Figure 3:
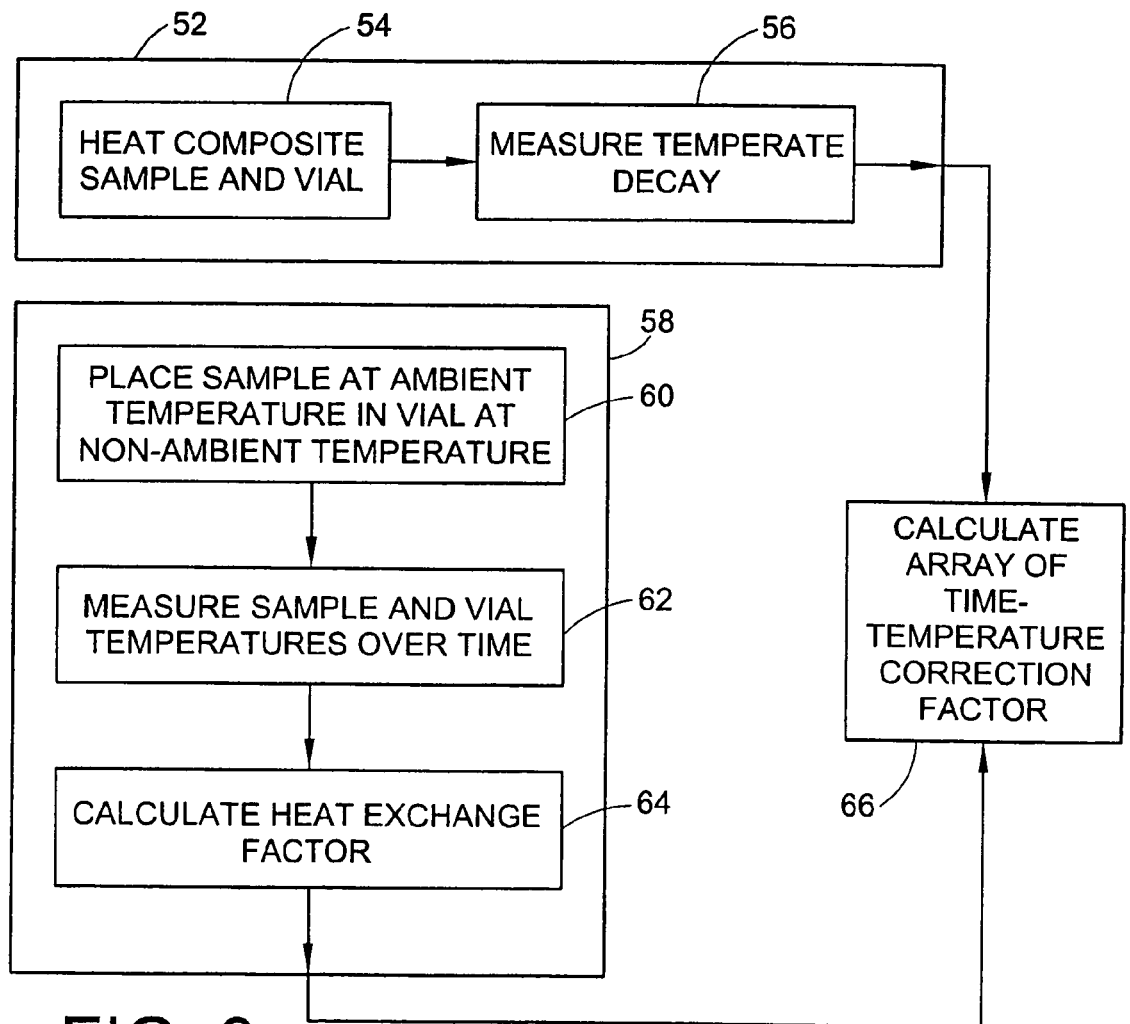
FIG. 3 is an intermediate level flow chart of the steps for determining a time-temperature correction factor for a sample in a container.

FIG. 2 depicts a top-level flow chart of an exemplary method in accordance with the teachings of the present invention for accurate determination of the temperature of the product in the container at the time of a NMR check weighing measurement. The first step 50 involves determining a time-temperature correction factor for a sample in a container that is to be tested. The intermediate steps of this determination is illustrated in FIG. 3, and includes in step 52 measuring the temperature decay for the composite sample and vial 22, determining in step 58 a heat exchange factor for the specific sample and vial 22 to be tested, and calculating in step 66 an array of time-temperature correction factors for the specific sample and vial 22 to be tested.

Measuring in step 52 the temperature decay for the composite sample and vial 22 is accomplished by altering the temperature of the composite sample and container from the ambient temperature, and measuring the temperature of the composite sample and container over time as the sample and container return to ambient temperature. One embodiment of step 52 includes the steps of heating the composite sample and vial to be tested in step 54 and, in step 56, measuring its temperature decay as the heated composite sample and vial are allowed to cool. The skilled artisan will appreciate that instead of measuring this temperature decay by heating the composite sample and vial above ambient temperature and letting it cool, the temperature decay may be found by cooling the composite sample and vial below ambient temperature and letting it warm.

Determining in step 58 a heat exchange factor for the specific sample and vial 22 to be tested includes the steps of placing the sample at an ambient temperature in a vial at a non-ambient temperature, as depicted in step 60, and measuring both the sample temperature and the vial 22 temperature as the sample and vial 22 are allowed to reach equilibrium, as shown in step 62. In step 64 a heat change factor, which may be referred to by the parameter alpha, is calculated for the sample and vial 22 to be tested having the relationship $$a = (m_s * C_s) / ((m_s * C_s) + (m_c * C_c))$$

where $m_s$ is the mass of the sample, $m_c$ is the mass of the container, $C_s$ is the heat capacity of the sample, and $C_c$ is the heat capacity of the container. Once the heat exchange factor is known for the specific sample and vial 22 to be tested, it may be combined with the time-temperature decay found in step 52 to provide an array of time-temperature correction factors, as seen in step 66.

An array of time-temperature correction factors may be determined to correct for temperature variations of a plurality of vials 22 filled simultaneously at filling station 25 using temperature measurements from a single vial 22 in the plurality of vials. This array may be calculated from the following relationships where: T(nccw) is the temperature of the sample at the location and time of magnetic resonance testing by the non-contact check weighing system; T(ir,g,x) is the temperature of the glass of vial 22 measured by a temperature sensor at array position x; T(ndl,x) is the temperature of the sample from a temperature sensor in the vial 22 at array position x; and, T(IR) is the temperature of the sample measured by a non-contact temperature sensor (such as an infrared sensor) at array position x. First, the general heat transfer between the sample and vial 22 is $$m_s * C_s * dT = m_c * C_c * dT$$

Combining these two relationships yields $$T(nccw) = a * T(ndl,x) + (1-a) * T(ir,g,x)$$

and $$dT = T(ndl,x) - T(ir,g,x)$$

The temperature of the sample decays exponentially with time as follows:

$$Tau = -(time)/LN[(T(IR) - T(nccw))/T(nld,x) - T(eq)]$$

Rearranging yields the relationship from which T(ndl,x) may be calculated for each location in the array $$T(time=y) = a*T(ndl,x) + (1-a)*T(ir,g,x) + [T(ndl,x) - a*T(ndl,x) - (1-a)*T(ir,g,x)] * e(-t/tau)$$

$$T(time=y) = a*T(ndl,x) + (1-a)*T(ir,g,x) + (1-a)[T(ndl,x) - T(ir,g,x)] * e(-t/tau)$$

$$T(ndl,x) = [-T(IR) + (1-a)*T(ir,g,x)*(I - e(-t/tau))] / [-a - (1-a)*e(-t/tau)]$$

Non-contact temperature measurement may be achieved with a variety of techniques. For example an infrared based pyrometer may be used to measure glass vial temperature prior to filling, and the temperature of the composite sample and vial. These pyrometers may be positioned in association with the filling needle structure to have a direct view of the vial contents. Further, temperature sensors may be placed in association with the first and last filling needles in the array to provide an indication of the temperature gradient between subsequent vial fills.

Figure 4:
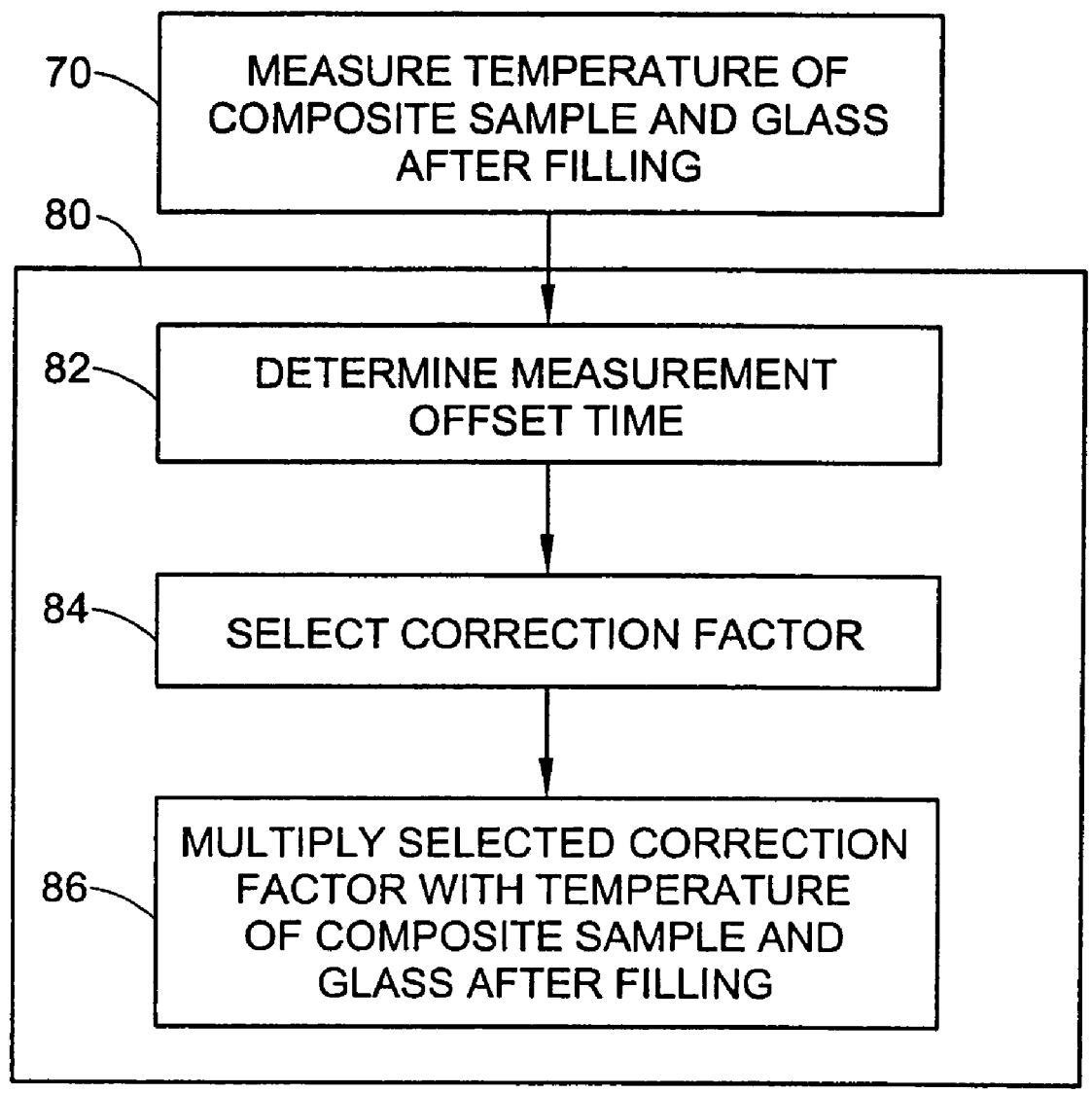
FIG. 4 is an intermediate level flow chart of the steps for applying the correction factor to the temperature of a sample and container measured other than at the time of an NMR check weight measurement.

FIG. 4 is an intermediate level flow chart of the steps for applying the correction factor to the temperature of a sample and container measured other than at the time of an NMR check weight measurement. Step 80 includes determining in step 82 the time interval between the time of magnetic resonance testing of the sample and the time of measuring the temperature of the sample, which may be called the measurement offset time, selecting the appropriate correction factor in step 84, and, in step 86, multiplying the selected correction factor with the temperature of the composite sample and vial 22 after filling.

The temperature of a plurality of composite samples and containers may also be corrected by the method of the present invention determining a temperature gradient for the plurality of composite samples and containers and applying the temperature gradient to the temperature of the plurality of composite samples and containers.

It will be understood that the embodiments described herein are merely exemplary and that a person skilled in the art may make many variations and modifications without departing from spirit and scope of the invention. The various embodiments may be practiced in the alternative, or in combination, as appropriate. All such modifications and variations are intended to be included within the scope of the invention as defined in the appended claims.

We claim:

1. A method for determining the temperature in a magnetic resonance check weighing system of a sample in a container on a production line at the time of magnetic resonance testing, comprising the steps of:
   determining a time-temperature correction factor for the sample in the container;
   measuring the temperature of the composite sample and the container at a time other than the time of magnetic resonance testing, and applying the correction factor to the temperature of the composite sample and container at a time other than the time of magnetic resonance testing.

2. The method according to claim 1, wherein said step of determining a time-temperature correction factor includes the step of measuring the composite sample and container temperature decay.

3. The method according to claim 2, wherein said step of measuring the composite sample and container temperature decay includes the steps of altering the temperature of the composite sample and container from the ambient temperature, and measuring the temperature of the composite sample and container over time as the sample and container return to ambient temperature.

4. The method according to claim 3, wherein said step of determining a time-temperature correction factor further includes the step of measuring the sample temperature and the container temperature as heat is transferred between the sample and the container.

5. The method according to claim 4, wherein step of measuring the composite sample and container temperature as heat is transferred between the sample and the container includes the step of placing the sample at ambient temperature in the container at non-ambient temperature.

6. The method according to claim 5, wherein said step of determining a time-temperature correction factor further includes the step of calculating a heat exchange factor for the sample and the container having the relationship $$(m_s * C_s)/((m_s * C_s) + (m_c * C_c))$$

where $/m_s$ is the mass of the sample, $m_c$ is the mass of the container, $C_s$ is the heat capacity of the sample, and $C_c$ is the heat capacity of the container.

7. The method according to claim 5, wherein said step of determining a time-temperature correction factor further includes the step of calculating an array of time-correction factors for a plurality of composite sample and container temperatures.

8. The method according to claim 1, wherein said step of measuring the temperature of the composite sample and container at a time other than the time of magnetic resonance testing is performed at a time proximate to substantial completion of filling of the container with the sample.

9. The method according to claim 1, wherein the time interval between the time of magnetic resonance testing of the sample and the time of measuring the temperature of the sample and the container is the measurement offset time, and further including the step of determining the measurement offset time, and said step of applying the correction factor includes the steps of selecting the correction factor for the sample and container at the measurement offset time, and multiplying the selected correction factor with the temperature of the composite sample and container at the time of measurement other than the time of magnetic resonance testing.

10. The method according to claim 1, further including the steps of measuring the temperature of a plurality of composite samples and containers other than at the time of magnetic resonance testing, and determining a temperature gradient for the plurality of composite samples and containers.

11. The method according to claim 10, wherein said step of applying the correction factor includes the step of applying the temperature gradient to the temperature of the plurality of composite samples and containers.

* * * * *